United States Patent [19]

Diamond et al.

[11] 4,169,106

[45] Sep. 25, 1979

[54] ANTIARRHYTHMIC N,N'-BIS(PHENYLCARBAMOYLALKYL-)AMIDINES

[75] Inventors: Julius Diamond, Mountain Lakes; Ronald A. Wohl, Morris Plains, both of N.J.

[73] Assignee: Cooper Laboratories, Inc., Parsippany, N.J.

[21] Appl. No.: 958,603

[22] Filed: Nov. 8, 1978

Related U.S. Application Data

[63] Continuation-in-part of Ser. No. 838,404, Sep. 30, 1977, abandoned.

[51] Int. Cl.$^2$ .................. A61K 31/165; C07C 103/76
[52] U.S. Cl. ..................... 260/558 A; 260/465 D; 260/559 A; 260/562 N; 424/304; 424/324

[58] Field of Search .......... 260/558 A, 559 A, 562 N, 260/465 D

[56] References Cited

U.S. PATENT DOCUMENTS

| | | | |
|---|---|---|---|
| 3,350,446 | 10/1967 | Bruce | 260/562 N X |
| 3,935,266 | 1/1976 | Hashimoto et al. | 260/558 A X |
| 4,041,072 | 8/1977 | Fauren et al. | 260/558 A |

*Primary Examiner*—Thomas Waltz
*Attorney, Agent, or Firm*—John J. Kolano; Thomas R. Boland

[57] ABSTRACT

Novel N,N'-bis(phenylcarbamoylalkyl)amidines having antiarrhythmic activity are disclosed. They are prepared by reacting an aminoalkanoylanilide with an active acid derivative such as an imidic acid ester or an alkyl orthoester.

9 Claims, No Drawings

ANTIARRHYTHMIC N,N'-BIS(PHENYLCARBAMOYLALKYL)AMIDINES

REFERENCE TO RELATED APPLICATION

The present application is a continuation-in-part of application Ser. No. 838,404 filed Sept. 30, 1977, and now abandoned.

BACKGROUND OF THE INVENTION

This invention relates to novel compounds useful for treating cardiac arrhythmias and more particularly to novel disubstituted amidines useful for treating cardiac arrhythmias.

Cardiac arrhythmia may be defined as a variation from the normal rhythm of the heart beat. Different types of arrhythmias are recognized according to the portion of the heart which is affected and the way in which the beat departs from the norm. Thus, atrial flutter and fibrillation, ventricular flutter and fibrillation, sinus tachycardia and bradycardia are representative arrhythmias.

Cardiac arrhythmias are usually treated by administering drugs which help to restore the normal heartbeat. Such drugs as quinidine, procainamide, lidocaine, and propranolol have been used with some success in treating cardiac arrhythmias. The prior art drugs, however, have not been completely satisfactory. Undesirable side effects such as gastrointestinal distress, hypotension, myocardial depression, respiratory depression, and central nervous system (CNS) stimulation or depression have occurred with some of them.

Accordingly it is an object of this invention to provide a new class of antiarrhythmic drugs. A further object is to provide novel disubstituted amidines useful in the treatment of cardiac arrhythmias.

SUMMARY OF THE INVENTION

The present invention relates to compounds having the following general formula:

wherein:
R = hydrogen, lower alkyl, $C_3$–$C_4$ cycloalkyl, lower alkenyl, $C_4$ cycloalkylalkyl;
Alk = alkylene containing up to 5 carbon atoms;
$R^2$ = hydrogen, lower alkyl, halo, trifluoromethyl, lower alkoxy, cyano;
$R^6$ = hydrogen, lower alkyl, halo, lower alkoxy;
$R^3$, $R^4$, $R^5$ = hydrogen, lower alkyl, lower alkoxy; with the proviso that no more than 3 of $R^{2-6}$ are other than hydrogen, and $R^6$ cannot be halo when $R^2$ is trifluoromethyl or cyano.

In the various terms above, "lower" indicates a radical containing 1–4 carbon atoms.

The pharmaceutically acceptable addition salts of these compounds with acids are also included in the invention.

The disubstituted amidines of this invention may be administered orally or parenterally.

DESCRIPTION OF THE PREFERRED EMBODIMENTS

Suitable groups for R include hydrogen, methyl, ethyl, n-propyl, isopropyl, n-butyl, isobutyl, sec-butyl, t-butyl, cyclopropyl, cyclobutyl, allyl, 2-butenyl, 3-butenyl, isobutenyl, and cyclopropylmethyl groups.

For Alk, the free valences in the alkylene group can be on the same or different carbon atoms. Examples of suitable groups are methylene, ethylidene, ethane-1,2-diyl, propane-1,2-diyl, propane-1,3-diyl, butane-1,3-diyl, butane-1,4-diyl and pentane-1,5-diyl.

Suitable groups for $R^2$ and $R^6$ include hydrogen, methyl, ethyl, n-propyl, isopropyl, n-butyl, isobutyl, sec-butyl, t-butyl, fluoro, chloro, bromo, iodo, trifluoromethyl, methoxy, n-propoxy, isopropoxy, n-butoxy, isobutoxy, sec-butoxy, t-butoxy, and cyano groups.

By combination of the various groups referred to above, various substituted phenyl groups are formed. Representative substituted phenyl groups include: phenyl, 2-methylphenyl, 2-(n-propyl)phenyl, 2-isopropylphenyl, 2-(n-butyl)phenyl, 2-isobutylphenyl, 2-(sec-butyl)phenyl, 2-(t-butyl)phenyl, 2,6-dimethylphenyl, 2,6-diethylphenyl, 2,6-di(n-propyl)phenyl, 2,6-diisopropylphenyl, 2,6-di(n-butyl)phenyl, 2,6-diisobutylphenyl, 2,6-di(sec-butyl)phenyl, 2,6-di(t-butyl)phenyl, 2-methyl-6-ethylphenyl, 2-methyl-6-(n-propyl)phenyl, 2-methyl-6-isopropylphenyl, 2-methyl-6-(n-butyl)phenyl, 2-methyl-6-isobutylphenyl, 2-methyl-6-(sec-butyl)phenyl, 2-methyl-6-(t-butyl)phenyl, 2-ethyl-6-(n-propyl)phenyl, 2-ethyl-6-isopropylphenyl, 2-ethyl-6-(n-butyl)phenyl, 2-ethyl-6-isobutylphenyl, 2-ethyl-6-(sec-butyl)phenyl, 2-ethyl-6-(t-butyl)phenyl, 2-(n-propyl)-6-isopropylphenyl, 2-(n-propyl)-6-(n-butyl)phenyl, 2-(n-propyl)-6-isobutylphenyl, 2-(n-propyl)-6-(sec-butyl)phenyl, 2-(n-propyl)-6-(t-butyl)phenyl, 2-isopropyl-6-(n-butyl)phenyl, 2-isopropyl-6-isobutylphenyl, 2-isopropyl-6-(sec-butyl)phenyl, 2-isopropyl-6-(t-butyl)phenyl, 2-(n-butyl)-6-isobutylphenyl, 2-(n-butyl)-6-(sec-butyl)phenyl, 2-(n-butyl)-6-(t-butyl)phenyl, 2-isobutyl-6-(sec-butyl)phenyl, 2-isobutyl-6-(t-butyl)phenyl, 2-(sec-butyl)-6-(t-butyl)phenyl, 2-fluorophenyl, 2-chlorophenyl, 2-bromophenyl, 2-iodophenyl, 2,6-difluorophenyl, 2,6-dichlorophenyl, 2,6-dibromophenyl, 2-fluoro-6-chlorophenyl, 2-fluoro-6-bromophenyl, 2-fluoro-6-iodophenyl, 2-chloro-6-bromophenyl, 2-chloro-6-iodophenyl, 2-bromo-6-iodophenyl, 2-chloro-6-methylphenyl, 2-chloro-6-ethylphenyl, 2-chloro-6-(n-propyl)phenyl, 2-chloro-6-isopropylphenyl, 2-chloro-6-(n-butyl)phenyl, 2-chloro-6-isobutylphenyl, 2-chloro-6-(sec-butyl)phenyl, 2-chloro-6-(t-butyl)phenyl, 2-trifluoromethylphenyl, 2-methyl-6-trifluoromethyl-phenyl, 2-ethyl-6-trifluoromethylphenyl, 2-(n-propyl)-6-trifluoromethylphenyl, 2-isopropyl-6-trifluoromethylphenyl, 2-(n-butyl)-6-trifluoromethylphenyl, 2-(t-butyl)-6-trifluoromethylphenyl, 2-methoxyphenyl, 2-ethoxyphenyl, 2-(n-propoxy)phenyl, 2-isopropoxyphenyl, 2-(n-butoxy)phenyl, 2-isobutoxyphenyl, 2-(sec-butoxy)phenyl, 2-(t-butoxy)phenyl, 2,6-dimethoxyphenyl, 2,6-diethoxyphenyl, 2,6-di(n-propoxy)phenyl, 2,6-diisopropoxyphenyl, 2,6-di(n-butoxy)phenyl, 2,6-di(t-butoxy)phenyl, 2-methoxy-6-methylphenyl, 2-methoxy-6-ethylphenyl, 2-methoxy-6-(n-propyl)phenyl, 2-methoxy-6-(n-butyl)phenyl, 2-methoxy-6-(t-butyl)phenyl, 2-ethoxy-6-methylphenyl, 2-ethoxy-6-ethylphenyl, 2-ethoxy-6-(n-butyl)phenyl, 2-isopropoxy-6-methylphenyl, 2-isopropoxy-6-ethylphenyl, 2-isopropoxy-6-(sec-butyl)phenyl, 2,3-dimethylphenyl, 2,4-dimethylphenyl, 2,5-dimethylphenyl, 2-ethyl-3-methylphenyl, 2-ethyl-4-methylphenyl, 2-ethyl-5-methylphenyl, 2-isopropyl-3-methylphenyl, 2-isopropyl-4-methylphenyl, 2,4-diethylphenyl, 2,5-diethylphenyl, 2,4,6-trimethylphenyl, 2,4,6-triethylphenyl, 2,6-diisopropyl-4-ethylphenyl, 2,6-dimethyl-4-methoxyphenyl, 2,6-dimethyl-4-ethoxyphenyl, 2-cyanophenyl, 2-cyano-6-methylphenyl, 2-cyano-6-ethylphenyl, 2-cyano-6-isopropylphenyl, 2-cyano-6-methoxyphenyl, 2-cyano-4-methyl-6-methoxyphenyl, and the like.

Preferred compounds are those in which Alk is methylene. Preferred groups for R are hydrogen and methyl; preferred for R² and R⁶ are methyl and ethyl; preferred for R³, R⁴ and R⁵ is hydrogen.

Thus the preferred substituted phenyl groups include 2,6-dimethylphenyl, and 2,6-diethylphenyl.

The preferred compounds of this invention are N,N'-bis[(2,6-dimethylphenyl)carbamoylmethyl]acetamidine, and N,N'-bis[(2,6-diethylphenyl)carbamoylmethyl]acetamidine.

The compounds of this invention can be prepared by reacting a substituted anilide with an ester of an imidic acid according to the reaction

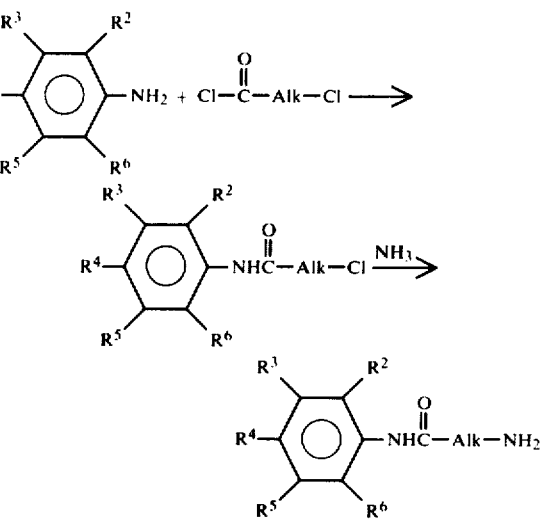

Alternatively, the substituted anilides may be prepared by reacting a suitably substituted aniline with an N-protected amino acid in the presence of a coupling reagent by the procedures well-known in peptide synthesis. The reaction may be represented as follows:

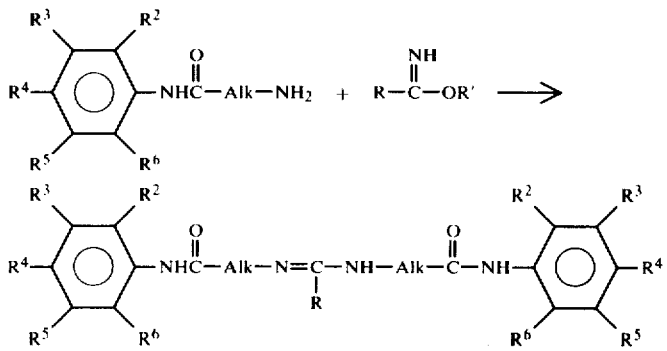

wherein Alk, R, R², R³, R⁴, R⁵ and R⁶ are defined as above and R' is alkyl containing up to 4 carbon atoms.

This reaction is conveniently carried out in an inert solvent, preferably ethanol, at a temperature of 20° to 80° C.

General procedures for synthesizing disubstituted amidines are described in Houben-Weyl, *Methoden der Organischen Chemie*, Stuttgart, 1958, Vol. 11, part 2, pp. 38–69; R. L. Shriner and F. W. Neumann, *Chem. Reviews*, 35, 365–372 (1944); P. A. Smith, *The Chemistry of Open-Chain Organic Nitrogen Compounds*, W. A. Benjamin, New York, 1965, Vol. I, pp. 177–193; Rodd, E. H., *Rodd's Chemistry of Carbon Compounds*, 2nd Ed., Elsevier Pub. Co., New York, Vol. Ic, pp. 110, 185–189, and E. C. Taylor and W. A. Erhardt, *J. Org. Chem.*, 1108–1112 (1963).

The intermediate substituted anilides may be prepared by reacting a suitably substituted aniline with a 2-haloalkanoyl halide such as 2-chloroacetyl chloride to form a substituted 2-haloalkanilide and subsequently reacting this compound with ammonia. This synthesis follows the following reaction scheme.

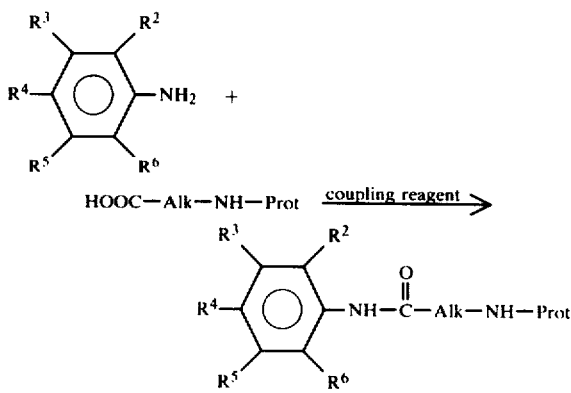

wherein Prot represents a conventional amine-protecting group, such as benzyloxycarbonyl, which is commonly used in peptide synthesis. Suitable coupling reagents are well-known in peptide synthesis and include, e.g., dicyclohexylcarbodiimide (DCC) and N-ethoxycarbonyl-2-ethoxy-1,2-dihydroquinoline (EEDQ).

After the synthesis has been accomplished, the protective group is removed by methods which are conventional in the art of peptide synthesis.

The procedures for synthesizing peptide linkages are described in detail in Houben-Weyl, *Methoden der Organischen Chemie*, Vol. 15, Thieme, Stuttgart, 1974.

Other methods for preparing the intermediate substituted anilides are disclosed in German Offenlegungsschrift No. 2,400,540.

The imidic acid esters used as intermediates in synthesizing the compounds of this invention can be prepared by reacting a nitrile with an alcohol by the following reaction

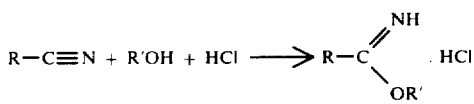

Imidate esters may also be prepared by reacting an amide silver salt with an alkyl iodide or by reacting an amide with a strong alkylating agent such as a Meerwein salt (e.g., a trialkyloxonium trifluoroborate). The synthesis of imidate esters is discussed in Roger, R. and Nielson, D. C., *Chem. Revs.*, 61, 179–201 (1961).

An alternative method of synthesizing the compounds of this invention is by reacting the intermediate substituted anilide with an alkyl orthoester according to the reaction

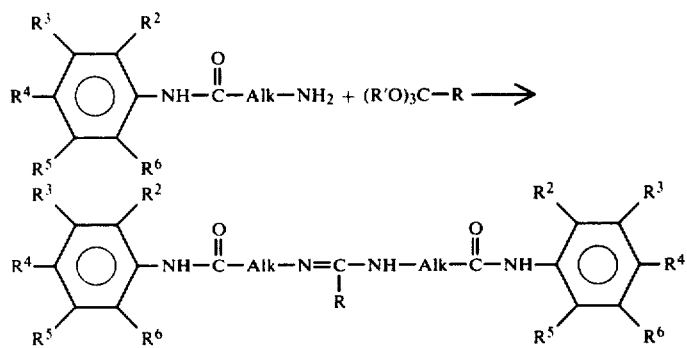

This reaction can be carried out in a suitable solvent such as ethanol at a temperature between 0° C. and 80° C. or, preferably, without using a solvent at temperatures between 80 and 160 C. It is advantageous to use up to 1 equivalent of acid as a catalyst in this reaction.

The ortho esters used as intermediates in synthesizing the compounds of this invention can be prepared from nitriles by the following series of reactions.

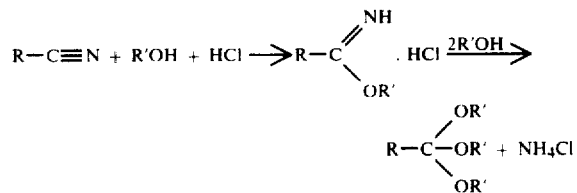

The preparation of such ortho esters is discussed in "Ortho Esters" in Sandler, S. R. and Karo, W., *Organic Functional Group Preparations*, Vol. II, Academic Press, New York, 1971. Detailed preparations for a number of ortho esters which are intermediates in preparing the disubstituted amidines of this invention are found in McElvain, S. M. and Nelson, J. W., *J. Amer. Chem. Soc.* 64, 1825–1827 (1942).

In further alternative methods for preparing the present compounds, the anilide of the formula

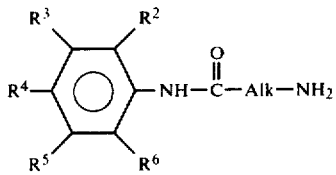

can be reacted with other active acid derivatives besides those described above. Thus, amide acetals of the formula

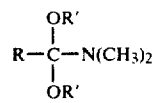

can be used in a process similar to that described above using imidate esters and ortho esters although this material is particularly reactive so that the reaction conditions would be milder. Dichloromethyl ethers of the formula Cl$_2$CHOR' can also be used in which case the reaction is carried out in the presence of a tertiary amine and the product obtained is a formamidine. This is a particularly useful method for the synthesis of such formamidines.

The compounds of this invention may be converted to their pharmaceutically acceptable acid addition salts by methods customary in the art. The pharmaceutically acceptable salts of this invention are those salts, the acid component of which is pharmacologically acceptable in the intended dosages. Suitable salts are those prepared from inorganic acids or organic acids. Such acids include: hydrochloric acid, hydrobromic acid, nitric acid, sulfuric acid, sulfamic acid, the polyphosphoric acids, phosphoric acid, glycerophosphoric acid, acetic acid, propionic acid, butyric acid, succinic acid, glycolic acid, 2,3-dihydroxypropionic acid, saccharic acid, gluconic acid, lactobionic acid, phenylacetic acid, cyclohexanecarboxylic acid, maleic acid, fumaric acid, lactic acid, citric acid, malic acid, camphoric acid, benzoic acid, tartaric acid, aspartic acid, salicyclic acid, phthalic acid, methanesulfonic acid, ethanesulfonic acid, benzenesulfonic acid, toluenesulfonic acid, nicotinic acid, ascorbic acid and the like. Preferred acids are hydrochloric, hydrobromic, acetic, benzoic and p-toluenesulfonic.

The compounds of this invention may possess one or more asymmetric carbon atoms. The groups R, Alk, and $R^{2-6}$ can contain asymmetric carbon atoms (e.g., when the substituent is sec-butyl). The presence of these asymmetric carbon atoms in general gives rise to optical activity, i.e., rotation of plane-polarized light passing through a solution of the material. When a single asymmetric carbon atom is present in the molecule, the compound will usually be obtained in the racemic modification, which consists of equimolar quantities of the dextrorotatory (+) and levorotatory (−) forms. These may be separated (resolved) by any of the known methods of resolution. In one method a salt of the optically active compound may be formed by reacting the racemic modification with an optically active acid, such as d-tartaric acid. Two products are obtained which, in general, have different properties and different solubilities and can accordingly be separated by fractional crystallization. After the salts are separated by fractional crystallization the pure (+) or (−) isomer of the compound is regenerated by removing the acid.

When Alk is a group such as ethylidene or propylene, the compounds of this invention possess two asymmetric carbon atoms. These asymmetric atoms are derived from the precursor substituted anilides. When the racemic modification of the precursor is used, containing equimolar proportions of D and L forms, three possible forms of the corresponding compound of the invention are obtained, the D,D, the L,L and the D,L forms. The D,D and L,L forms are optical isomers (enantiomers) and have identical physical properties except for their rotation of polarized light. Thus, together they constitute a racemic modification of the compound. The D,L form is an optically inactive (meso) form and, in general, has properties different from those of the D,D and L,L forms. The D,L form may thus be separated from the racemic modification by conventional means, and the racemic modification may be resolved by the procedures referred to above.

However, if the precursors are used in the optically pure form (D or L), only a single form (the D,D or L,L) of the compound of the invention will be formed, and no separation will be required. The optically pure substituted anilides may be prepared by resolving the racemic modification by the procedures described above or by asymmetric synthesis. The asymmetric synthesis is carried out by the procedure described above starting from a suitably substituted aniline and an optically pure (D or L) form of an amino acid. Since the procedure using optically pure reagents produces optically pure compounds at each stage of the synthesis, and since optically pure amino acids are relatively easily obtained, this synthesis procedure is preferred.

It is to be understood that all optical isomers are included within the scope of this invention.

The compounds of this invention are useful as antiarrhythmic agents. When used for this purpose, the compounds can be administered by the usual pharmaceutical procedures such as orally or parenterally. They can be combined with the customary pharmaceutical excipients and incorporated into the usual dosage forms such as tablets, capsules, and the like.

The antiarrhythmic utility of the compounds of this invention can be demonstrated by their effect against different types of cardiac arrhythmias in standard test procedures. Thus, the effectiveness of the compounds against ouabain-induced ventricular tachycardia was evaluated by the following procedure.

Mongrel dogs of either sex weighing between 7 and 12 kg were anesthetized with sodium pentobarbital, 30 mg/kg, i.v. The femoral artery was cannulated and arterial blood pressure measured via a pressure transducer connected to a strip chart recorder. Mean arterial pressure was derived electronically. The right vagus nerve was sectioned and its distal end stimulated at a frequency of 50 cycles per second. The stimulation voltage was determined for each animal prior to drug administration and was in the range of 3 to 4 volts. Throughout the experiment, Lead II electrocardiogram was continuously recorded.

The antiarrhythmic activity of compounds of this invention and standard compounds was also determined according to a modification of the method of Lucchesi and Hardman J. Pharmacol. Exp. Therap., 13, 372–81, 1961. Ouabain was injected at a dose of 40 $\mu$g/kg followed in 30 minutes by injections of 10 $\mu$g/kg every 15 minutes until ventricular or nodal tachycardia occurred. The arrhythmia was shown to be independent of the sino-atrial pacemaker by the failure of right vagal stimulation to alter its rate. The ventricular rhythm was allowed to continue for 20 minutes and then the test drugs were administered. In control dogs, the untreated arrhythmia persisted for at least two hours.

Test drugs were administered by titration until the arrhythmia was reversed. The criteria for antiarrhythmic activity were:

(1) Reversion to normal sinus rhythm within a few minutes following drug administration (i.v.)
(2) Maintenance of sinus rhythm for 30 minutes or longer.
(3) Failure of right vagal stimulation to trigger ectopic ventricular beats.

In some of the animals, return of arrhythmia was produced by administering 40 units of intravenous insulin in order to demonstrate the continued presence of ouabain in sufficient concentrations to induce cardiac toxicity.

For intravenous administration drugs were dissolved in physiologic saline and given in a volume of 0.1 ml/kg. For oral administration drugs were delivered through a tube positioned in the stomach. For intraduodenal administration the abdomen was opened and a catheter positioned directly into the duodenum.

The effectiveness of the compounds against acetylcholine-induced ventricular fibrillation was determined by the following procedure.

Mongrel dogs unselected as to age or sex and ranging from 10 to 15 kg in weight were anesthetized by an intravenous injection of pentobarbital sodium, 30 mg/kg. In each dog a polyethylene cannula was inserted into the left femoral artery and connected to a transducer for blood pressure measurements. The left femoral vein was also catheterized for the purpose of drug injections. Artificial ventilation with room air was maintained by a Harvard positive-pressure respirator through a cuffed endotracheal tube.

Lead II electrocardiograms were monitored continuously on an oscilloscope and all recordings were made on an eight channel strip chart recorder.

After a mid-sternal thoracotomy, the pericardium was reflected from the right atrium and sutured to the thoracic wall to form a cradle. Selective atrial fibrillation was induced by applying a few drops of a 4% aqueous solution of acetylcholine directly to the right atrium through a 20 gauge needle spatula. The duration of atrial fibrillation was determined by noting on the electrocardiogram the time required for sinus rhythm to reappear.

After two control periods of fibrillation were obtained, drugs were then administered either intravenously, orally, or intraduodenally. Attempts were then made to reinduce atrial fibrillation at the following time intervals: 15, 30, 60 and 120 minutes after drug administration. A given dose of a drug was considered to be active if it significantly reduced the duration of the atrial arrhythmia at any of the above time intervals.

All drugs were administered as the free base and the results were analyzed by Student's "t" test.

The effect of the compounds against ventricular arrhythmias after coronary ligation simulating myocardial infarction was determined by the following procedure.

Experimental myocardial infarction was produced in mongrel dogs (10–15 kg) under general anesthesia with sodium pentobarbital, 30 mg/kg, i.v., and under artificial respiration maintained with a Harvard positive-pressure respirator. Under aseptic conditions, the thorax was opened at the fourth intercostal space. The pericardium was incised and the anterior descending branch of the left coronary artery was dissected free about 8 mm distal to the edge of the left atrial appendage. Two silk ligatures were passed under the artery and the vessel was ligated in two stages according to the method described by A. S. Harris, Circulation 1, 1318 (1950). After closure of the pericardium and the thorax and when the respiration became spontaneous, the animal was maintained under supervision until awakening, 3 to 4 hours later.

The following day, eighteen hours post-surgery, the animals presented with a permanent extrasystolic arrhythmia. This arrhythmia was quantitated by counting every heart beat during a 5-minute period and noting the number of normal and abnormal depolarizations. All animals were studied in the unanesthetized state. Lead III electrocardiogram was continuously recorded while the animals were supported in a harness and maintained in a quiet environment. These animals were trained prior to surgery to lie quietly while ECG recordings were made. Drugs to be studied were injected directly into the brachial vein or were given orally contained in gelatin capsules. The criteria for inclusion into the study were as follows:

(1) The number of ectopic beats should be greater than 30% of the total number of beats per minute.
(2) The frequency of abnormal beats should remain constant for a two-hour monitoring period prior to drug administration.

After drug administration, the ECG was taken at 15-minute intervals for at least 4 hours. Results were recorded as percent reduction in the number of ectopic beats.

All of the compounds of this invention showed some antiarrhythmic activity in at least one of the above procedures.

The following examples are intended to illustrate the practice of this invention without limiting its scope.

EXAMPLE I

N,N'-bis [(2,6-dimethylphenyl)carbamoylmethyl]acetamidine hydrochloride (hydrate)

4.85 Grams (0.039 mole) of ethyl acetimidate hydrochloride and 7.0 g of 2-amino-2',6'-dimethylacetanilide were dissolved in 75 ml of anhydrous ethanol and stirred at room temperature for two days. The solid which formed was collected on a filter, recrystallized from ethanol, and dried overnight under vacuum at 60° C. M.P. 240°–241° C.

EXAMPLE II

This example illustrates another process for preparing N,N'-bis[(2,6-dimethylphenyl)carbamoylmethyl]acetamidine hydrochloride.

10 Grams (0.056 mole) of 2-amino-2'6'-dimethylacetanilide and 5.14 ml (4.55 g, 0.028 mole) of triethyl orthoacetate were combined and heated in an oil bath at 100° C. for 1 hour. The residue was triturated with diethyl ether and the solid was collected on a filter and air dried. About 7 grams of the solid were slurried in methanol and concentrated hydrochloric acid was added until all the solid had dissolved and the pH was 1.0. The methanol was removed under vacuum and the residue was triturated with diethyl ether, dried, and recrystallized from methanol. M.P. 242°–244° C.

EXAMPLE III

This example illustrates the synthesis of N,N'-bis[(2,6-diethyl)carbamoylmethyl]acetamidine hydrochloride.

To 89.54 grams (0.6 mole) of 2,6-diethylaniline dissolved in 509 milliliters of glacial acetic acid was added 74.54 grams (0.66 mole) of chloroacetyl chloride dissolved in 240 milliliters of acetone, and the mixture was stirred at room temperature for 1½ hours. Then 196.78 grams of sodium acetate dissolved in about 500 milliliters of water was added and the mixture was stirred for another hour. The product was precipitated by adding more water. The solid precipitate was collected by filtration, washed with water and dried overnight under vacuum at 60° C. M.P. 135°–136° C. 51.92 Grams (0.23 mole) of the material prepared above was slurried in a mixture of 285 milliliters of ethanol and 15 milliliters of water and cooled in a dry ice/acetone bath. Ammonia gas was bubbled into the mixture until it was saturated, and the mixture was put into pressure bottles and allowed to stand for six days. The mixture was then cooled in a dry ice/acetone bath and filtered. The filtrate was evaporated under vacuum and the residue was triturated with chloroform, collected by filtration and air dried. 42.0 Grams of this material was slurried in 300 milliliters of ice water and 150 milliliters of chloroform were added. The mixture was shaken vigorously. Five milliliters of 2 N aqueous sodium hydroxide solution were added in portions, with shaking after each addition. The aqueous layer was extracted with two 100 milliliter portions of chloroform. The portions of chloroform were combined, dried over potassium carbonate, and the chloroform was removed under vacuum. The product solidified on cooling and was dried for five hours under vacuum at room temperature to yield 2-amino-2',6'-diethylacetanilide. M.P. 70°–71° C.

10 Grams (0.048 mole) of 2-amino-2',6'-diethylacetanilide and 4.44 milliliters (3.93 grams, 0.024 mole) of triethyl orthoacetate were combined and heated in an oil bath at 100° C. for one hour. The residue was allowed to cool to room temperature and the gummy solid which was obtained was triturated with ether. The crude free base obtained was converted to the salt as in Example II. The product was recrystallized twice from acetonitrile to yield N,N'-bis[(2,6-diethylphenyl)carbamoylmethyl]acetamidine hydrochloride. M.P. 187°-189° C.

EXAMPLE IV

This example illustrates another procedure for synthesizing a compound of this invention.

0.82 Grams (4.13 millimoles) of 2-aminoacetanilide hydrochloride, 0.77 g (4.13 millimoles) of 2-aminoacetanilide (free base) were dissolved in 1.4 milliliters of hot methanol. To this solution was added 0.76 milliliters (0.67 g, 4.13 millimoles) of triethyl orthoacetate. The mixture was heated gently for five minutes. The reaction mixture was cooled and the reaction product precipitated by addition of diethyl ether. The supernatant liquid was decanted, and the precipitate was triturated with ether and collected on a filter. The product was recrystallized from ethanol, and dried to yield about 300 milligrams of N,N'-bis[phenylcarbamylmethyl]acetamidine hydrochloride.

EXAMPLE V

This example illustrates the preparation of other compounds of this invention.

By the procedures of Example III, substituted anilines listed in Table I are converted into the listed intermediate substituted anilides, and these in turn are converted into the N,N'-disubstituted amidines of the invention, by the procedure of Example III or IV.

TABLE I

| Aniline | Acetanilide | N,N'-disubstituted amidine |
|---|---|---|
| aniline | 2-aminoacetanilide | N,N'-bis(phenylcarbamoylmethyl)acetamidine hydrochloride |
| 2,6-diisopropylaniline | 2-amino-2',6'-diisopropylacetanilide | N,N'-bis[(2,6-diisopropylphenyl)-carbamoylmethyl]acetamidine hydrochloride |
| 2-fluoroaniline | 2-amino-2'-fluoroacetanilide | N,N'-bis[(2-fluorophenyl)carbamoylmethyl]-acetamidine hydrochloride |
| 2-chloroaniline | 2-amino-2'-chloroacetanilide | N,N'-bis[(2-chlorophenyl)carbamoylmethyl]-acetamidine hydrochloride |
| 2-bromoaniline | 2-amino-2'-bromoacetanilide | N,N'-bis[(2-bromophenyl)carbamoylmethyl]-acetamidine hydrochloride |
| 2-iodoaniline | 2-amino-2'-iodoacetanilide | N,N'-bis[(2-iodophenyl)carbamoylmethyl]-acetamidine hydrochloride |
| o-toluidine | 2-amino-2'-methylacetanilide | N,N'-bis[(2-methylphenyl)carbamoylmethyl]-acetamidine hydrochloride |
| 2-ethylaniline | 2-amino-2'-ethylacetanilide | N,N'-bis[(2-ethylphenyl)carbamoylmethyl]-acetamidine hydrochloride |
| 2,6-dichloroaniline | 2-amino-2',6'-dichloroacetanilide | N,N'-bis[(2,6-dichlorophenyl)carbamoylmethyl]-acetamidine hydrochloride |
| 2,6-dibromoaniline | 2-amino-2',6'-dibromoacetanilide | N,N'-bis[(2,6-dibromophenyl)carbamoylmethyl]-acetamidine hydrochloride |
| 6-ethyl-o-toluidine | 2-amino-6'-ethyl-2'-methylacetanilide | N,N'-bis[(6-ethyl-2-methylphenyl)carbamoylmethyl]-acetamidine hydrochloride |
| 2-chloro-6-methylaniline | 2-amino-2'-chloro-6'-methylacetanilide | N,N'-bis[(2-chloro-6-methylphenyl)-carbamoylmethyl]acetamidine hydrochloride |
| o-anisidine | 2-amino-2'-methoxyacetanilide | N,N'-bis[(2,6-dimethoxyphenyl)-carbamoylmethyl]acetamidine hydrochloride |
| anthranilonitrile (2-cyanoaniline) | 2-amino-2'-cyanoacetanilide | N,N'-bis[(2-cyanophenyl)carbamoylmethyl]-acetamidine hydrochloride |
| 2-aminobenzotrifluoride (2-trifluoromethylaniline) | 2-amino-2'-trifluoromethylacetanilide | N,N'-bis[(2-trifluoromethylphenyl)carbamoyl-methyl]acetamidine hydrochloride |
| m-toluidine | 2-amino-3'-methylacetanilide | N,N'-bis[(3-methylphenyl)carbamoyl-methyl]acetamidine hydrochloride |
| p-toluidine | 2-amino-4'-methylacetanilide | N,N'-bis[(4-methylphenyl)carbamoyl-methyl]acetamidine hydrochloride |
| 4-(n-butyl)aniline | 2-amino-4'-butylacetanilide | N,N'-bis[(4-butylphenyl)carbamoyl-methyl]acetamidine hydrochloride |
| 4-isopropylaniline | 2-amino-4'-isopropylacetanilide | N,N'-bis[(4-isopropylphenyl)-carbamoylmethyl]acetamidine hydrochloride |
| 2-fluoro-4-methylaniline | 2-amino-2'-fluoro-4'-methylacetanilide | N,N'-bis[(2-fluoro-4-methylphenyl)-carbamoylmethyl]acetamidine hydrochloride |
| 2-chloro-4-methylaniline | 2-amino-2'-chloro-4'-methylacetanilide | N,N'-bis[(2-chloro-4-methylphenyl)-carbamoylmethyl]acetamidine hydrochloride |
| 2-methoxy-5-methylaniline | 2-amino-2'-methoxy-5'-methylacetanilide | N,N'-bis[(2-methoxy-5-methylphenyl)-carbamoylmethyl]acetamidine hydrochloride |
| 2,3-dimethylaniline | 2-amino-2',3'-dimethylacetanilide | N,N'-bis[(2,3-dimethylphenyl)carbamoylmethyl]-acetamidine hydrochloride |
| 2,4-dimethylaniline | 2-amino-2',4'-dimethylacetanilide | N,N'-bis[(2,4-dimethylphenyl)carbamoylmethyl]-acetamidine hydrochloride |
| 2,5-dimethylaniline | 2-amino-2',5'-dimethylacetanilide | N,N'-bis[(2,5-dimethylphenyl)carbamoylmethyl]-acetamidine hydrochloride |
| m-anisidine | 2-amino-3'-methoxyacetanilide | N,N'-bis[(3-methoxyphenyl)carbamoylmethyl]-acetamidine hydrochloride |
| p-anisidine (4-methoxyaniline) | 2-amino-4'-methoxyacetanilide | N,N'-bis[(4-methoxyphenyl)carbamoylmethyl]-acetamidine hydrochloride |
| 4-ethoxyaniline | 2-amino-4'-ethoxyacetanilide | N,N'-bis[(4-ethoxyphenyl)carbamoylmethyl] - acetamidine hydrochloride |
| 4-aminoveratrole (3,4-dimethoxyaniline) | 2-amino-3',4'-dimethoxyacetanilide | N,N'-bis[(3,4-dimethoxyphenyl)carbamoylmethyl]-acetamidine hydrochloride |
| 2,4,6-trimethylaniline | 2-amino-2',4',6'-trimethylacetanilide | N,N'-bis[(2,4,6-trimethylphenyl)-carbamoylmethyl]acetamidine hydrochloride |
| 3,4,5-trimethoxyaniline | 2-amino-3',4',5'-trimethoxyacetanilide | N,N'-bis[(3,4,5-trimethoxyphenyl)-carbamoylmethyl]acetamidine hydrochloride |
| 2-chloro-5-methoxyaniline | 2-amino-2'-chloro-5'-methoxyacetanilide | N,N'-bis[(2-chloro-5-methoxyphenyl)carbamoyl- |

TABLE I-continued

| Aniline | Acetanilide | N,N'-disubstituted amidine |
|---|---|---|
| | | methyl]acetamidine hydrochloride |
| 2,6-dimethylaniline | 3-amino-2',6'-dimethylpropionanilide | N,N'-bis[2-((2,6-dimethylphenyl)carbamoyl)ethyl]-acetamidine hydrochloride |
| 2,6-dimethylaniline | 4-amino-2',6'-dimethylbutyranilide | N,N'-bis[3-((2,6-dimethylphenyl)carbamoyl)propyl]-acetamidine hydrochloride |

EXAMPLE VI

This example illustrates the synthesis of compounds of this invention having varied R groups.

By the process of Example II, using the orthoesters listed in Table II in place of triethyl orthoacetate, the corresponding compounds listed in the Table II were prepared.

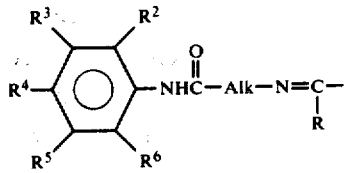

TABLE II

| Orthoester | N,N'-bis(phenylcarbamoylmethyl)amidine |
|---|---|
| triethyl orthopropionate | N,N'-bis[(2,6-dimethylphenyl)carbamoylmethyl]propionamidine hydrochloride |
| triethyl orthobutyrate | N,N'-bis[(2,6-dimethylphenyl)carbamoylmethyl]butyramidine hydrochloride |
| triethyl orthoisobutyrate | N,N'-bis[(2,6-dimethylphenyl)carbamoylmethyl]isobutyramidine hydrochloride |
| triethyl orthopentanoate | N,N'-bis[(2,6-dimethylphenyl)carbamoylmethyl]pentanamidine hydrochloride |
| triethyl orthoisovalerate (1,1,1-triethoxy-3-methylbutane) | N,N'-bis[(2,6-dimethylphenyl)carbamoylmethyl]-3-methylbutanamidine hydrochloride |
| triethyl orthocyclopropanecarboxylate | N,N'-bis[(2,6-dimethylphenyl)carbamoylmethyl]cyclopropane-carboxamidine hydrochloride |
| triethyl 2-(cyclopropyl)orthoacetate [(2,2,2-triethoxyethyl)cyclopropane] | N,N'-bis[(2,6-dimethylphenyl)carbamoylmethyl]cyclopropane-acetamidine hydrochloride |

EXAMPLE VII

This example illustrates the synthesis of compounds of this invention wherein R=H.

By the process of Example II, using triethyl orthoformate in place of triethyl orthoacetate, and using the substituted 2-aminoacetanilides listed in Table III, the corresponding N,N'-disubstituted formamidines of this invention listed in the table were prepared.

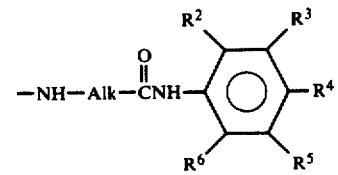

TABLE III

| Substituted acetanilide | N,N'-disubstituted amidine |
|---|---|
| 2-amino-2'-methylacetanilide | N,N'-bis[(2-methylphenyl)carbamoylmethyl]formamidine hydrochloride |
| 2-amino-2',6'-dimethylacetanilide | N,N'-bis[(2,6-dimethylphenyl)carbamoylmethyl]-formamidine hydrochloride |
| 2-amino-2',6'-diethylacetanilide | N,N'-bis[(2,6-diethylphenyl)carbamoylmethyl]-formamidine hydrochloride |
| 2-amino-2',6'-diisopropylacetanilide | N,N'-bis[(2,6-diisopropylphenyl)carbamoylmethyl]-formamidine hydrochloride |

EXAMPLE VIII

A solution of 3.0 grams of 2-amino-2',6'-dimethylacetanilide and 1.56 grams of tri-n-butylamine in 35 ml. of dry tetrahydrofuran was cooled in an ice bath and a solution of 0.97 grams of α,α-dichloromethyl ether in 5 ml. of dry tetrahydrofuran was added dropwise. The mixture was then allowed to warm to room temperature and it was stirred at that temperature for 20 hours. The white solid which formed was separated by filtration and recrystallized from methanol to give N,N'-bis[(2,6-dimethylphenyl)carbamoylmethyl]formamidine hydrochloride melting at about 235°-240° C. with decomposition.

We claim:

1. A compound having the formula wherein:

R=hydrogen, lower alkyl, $C_3-C_4$ cycloalkyl, lower alkenyl, $C_4$ cycloalkylalkyl;

Alk=alkylene containing up to 5 carbon atoms;

$R^2$=hydrogen, lower alkyl, halo, $CF_3$, lower alkoxy, cyano;

$R^6$=hydrogen, lower alkyl, halo, lower alkoxy;

$R^3$, $R^4$, $R^5$=hydrogen, lower alkyl, lower alkoxy; with the proviso that no more than 3 of $R^{2-6}$ are other than hydrogen and $R^6$ cannot be halo when $R^2$ is trifluoromethyl or cyano; and pharmaceutically acceptable addition salts with acids.

2. A compound according to claim 1 having the formula

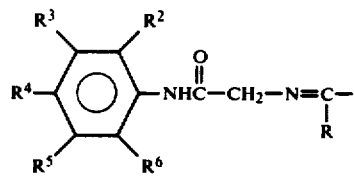

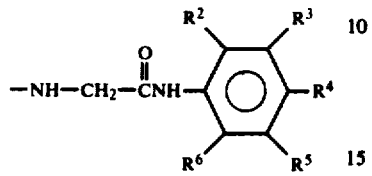

wherein:

R = hydrogen, lower alkyl, C₃-C₄ cycloalkyl, lower alkenyl and C₄ cycloalkylalkyl;

R² = hydrogen, lower alkyl, halo, CF₃, lower alkoxy, cyano;

R⁶ = hydrogen, lower alkyl, halo, lower alkoxy;

R³, R⁴, R⁵ = hydrogen, lower alkyl, lower alkoxy; with the proviso that no more than 3 of R²⁻⁶ are other than hydrogen and R⁶ cannot be halo when R² is trifluoromethyl or cyano; and pharmaceutically acceptable addition salts with acids.

3. A compound according to claim 2 wherein R is methyl.

4. A compound according to claim 2 wherein R³, R⁴, and R⁵ are hydrogen.

5. A compound according to claim 1 having the formula

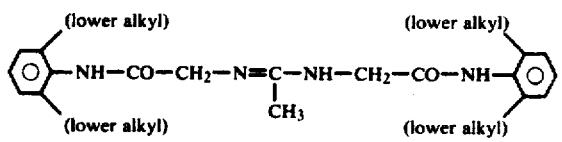

6. N,N'-Bis[(2,6-dimethylphenyl)carbamoylmethyl]acetamidine and pharmaceutically acceptable acid addition salts.

7. N,N'-Bis[(2,6-diethylphenyl)carbamoylmethyl]acetamidine and pharmaceutically acceptable acid addition salts.

8. N,N'-Bis[(2,6-diisopropylphenyl)carbamoylmethyl]acetamidine and pharmaceutically acceptable acid addition salts.

9. N,N'-Bis(phenylcarbamoylmethyl)acetamidine and pharmaceutically acceptable acid addition salts.

* * * * *